United States Patent [19]
Gadient et al.

[11] 4,272,533
[45] Jun. 9, 1981

[54] N-PHENYLINDOLINE DERIVATIVES, AND PHARMACEUTICAL COMPOSITIONS CONTAINING THEM

[75] Inventors: Fulvio Gadient, Birsfelden; Rudolf Süess, Bettingen, both of Switzerland

[73] Assignee: Sandoz Ltd., Basel, Switzerland

[21] Appl. No.: 70,266

[22] Filed: Aug. 27, 1979

[30] Foreign Application Priority Data

Aug. 30, 1978 [CH] Switzerland .......................... 9155/78

[51] Int. Cl.³ ..................... A61K 31/40; C07D 209/14
[52] U.S. Cl. ............................... 424/248.4; 260/245.7; 260/326.11R; 424/248.58; 424/250; 424/267; 424/274; 544/143; 544/144; 544/373; 546/201
[58] Field of Search .................... 260/326.11 R, 245.7; 544/373, 143, 144; 424/248.4, 248.58, 250, 267, 274; 546/201

[56] References Cited

U.S. PATENT DOCUMENTS 3,644,403  2/1972  Canas-Rodriguez et al. ....... 544/373

FOREIGN PATENT DOCUMENTS 2081318  10/1974  France .

OTHER PUBLICATIONS

Ganellin et al., J. Chem. Soc. (C), 1969, pp. 1537–1540.
Canas-Rodriguez et al., J. Med. Chem., 1972, vol. 15, No. 7, pp. 762–770.

Primary Examiner—Paul M. Coughlan, Jr.
Attorney, Agent, or Firm—Gerald D. Sharkin; Robert S. Honor

[57] ABSTRACT 2-aminoethyl-1-phenylindolines are useful as anti-diabetic and anti-obesity agents.

12 Claims, No Drawings

N-PHENYLINDOLINE DERIVATIVES, AND PHARMACEUTICAL COMPOSITIONS CONTAINING THEM

This invention relates to N-phenylindoline derivatives, their production and pharmaceutical compositions containing them.

The present invention provides in one aspect 2-aminoethyl-1-phenyl-indolines, hereinafter referred to as compounds of the invention.

Each of the benzene rings may be substituted or unsubstituted. The amino group of the aminoethyl group may be a primary, secondary or tertiary amine and the ethylene moiety may bear substituents, e.g. a methyl group. The 3 position of the indoline nucleus may be substituted e.g. with alkyl.

More particularly the present invention provides compounds of formula I

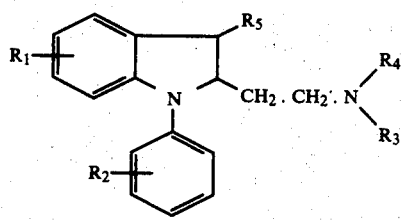

wherein
$R_1$ and $R_2$ independently are hydrogen, halogen of atomic number from 9 to 35, alkoxy ($C_{1-4}$) or alkyl ($C_{1-4}$),
$R_3$ and $R_4$ either are independently hydrogen or alkyl ($C_{1-6}$), or together with the nitrogen atom to which they are bound form a pyrrolidino, piperidino, perhydroazepino, morpholino or 4-alkyl($C_{1-4}$)-piperazino radical, and
$R_5$ is hydrogen or alkyl($C_{1-4}$).

In the formula I when $R_5$ is alkyl, the hydrogen atoms at C-2 and C-3 may be cis or trans to each other and conveniently they are trans to each other.

Any carbon containing radical has preferably 1 or 2 carbon atoms, or especially 1 carbon atom. $R_1$ is conveniently in the 5 position. $R_1$ and $R_2$ are conveniently hydrogen or alkyl and especially hydrogen; conveniently they are identical. $R_2$ is conveniently in the para position. $R_3$ and $R_4$ are conveniently other than hydrogen. $R_3$ and $R_4$ together with the nitrogen atom to which they are bound are conveniently pyrrolidino.

The compounds of the invention may be obtained in conventional manner, e.g. by reducing an appropriate 2-aminoethyl-1-phenylindole, and if desired converting the resulting 2-aminoethyl-1-phenylindoline into another 2-aminoethyl-1-phenylindoline.

As an example of one interconversion route, a 2-alkylmethyl- or -alkylbenzyl-aminoethyl-1-phenylindoline is converted into a 2-alkylaminoethyl-1-phenylindoline by splitting the methyl or benzyl group off by treatment with a chloroformate producing a carbamate and splitting the carbamate.

The present invention also provides a process for the production of a compound of formula I as defined above which comprises
(a) reducing a compound of formula II

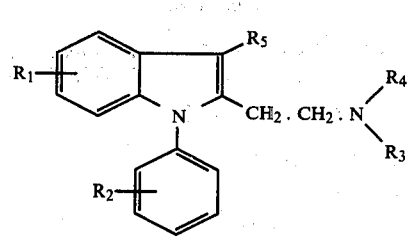

wherein $R_1$ to $R_5$ are as defined above, or
(b) splitting off the $COOR_6$ radical from a compound of

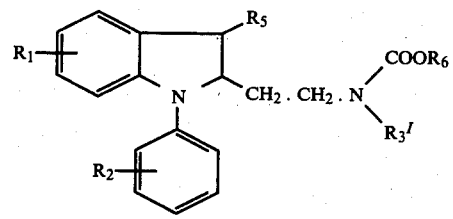

wherein
$R_1$, $R_2$ and $R_5$ are as defined above, and
$R_3{}^I$ is alkyl($C_{1-6}$) and
$R_6$ is alkyl($C_{1-4}$), phenyl or benzyl,
to produce a compound of formula I wherein
$R_3$ is alkyl($C_{1-6}$) and
$R_4$ is hydrogen.

The reduction may be effected in conventional manner for the reduction of an indole to an indoline. The conditions may be chosen to favour formation of trans compounds, e.g. with nascent hydrogen from e.g. lithium, sodium or potassium in ammonia, or cis compounds, e.g. with a diborane or a complex borohydride such as sodium borohydride/boron trifluoride or a borane/dimethylsulphide complex. Naturally mixtures of cis and trans isomers of formula I may be formed, which may be separated in conventional manner.

Process (b) may be effected in conventional manner for the splitting of a carbamate to produce a secondary amine, e.g. with a mineral acid e.g. HCl or an alkali metal hydroxide e.g. KOH or NaOH. When $R_6$ is benzyl, the carbamate may alternatively be split using catalytic hydrogenation e.g. under mild conditions using palladium catalysts.

The starting materials may be made in conventional manner as follows:

(a) Compounds of formula II wherein $R_5{}^I$=alkyl($C_{1-4}$):

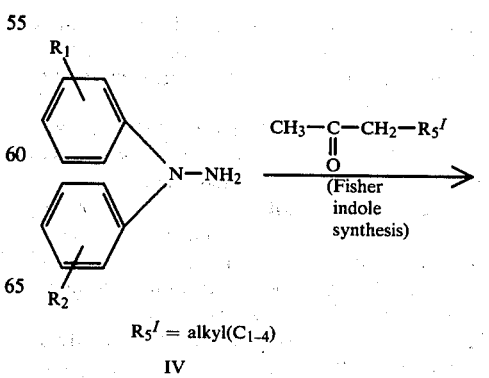

$R_5{}^I$ = alkyl($C_{1-4}$)

IV

-continued

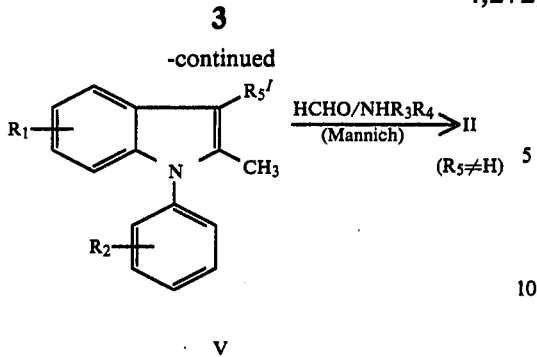

(b) Compounds of formula II wherein $R_3=R_4=H$:

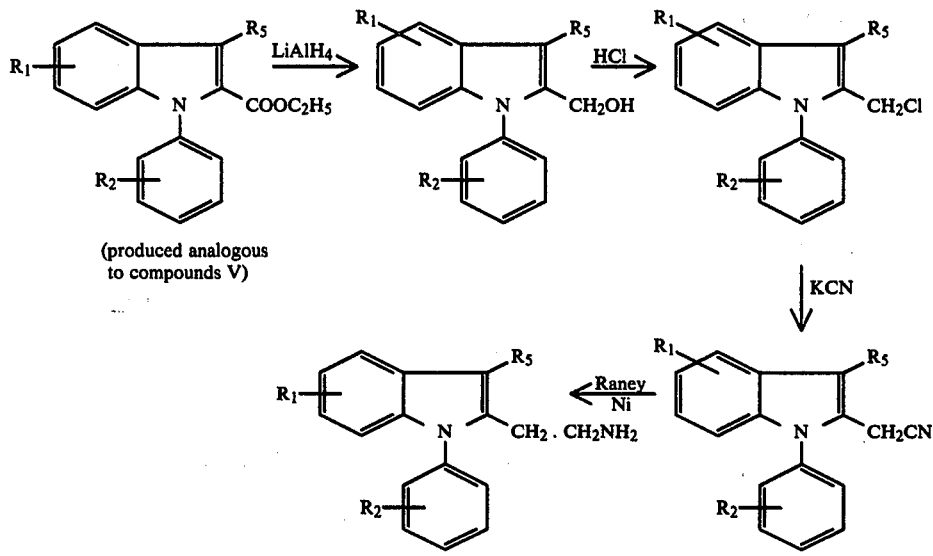

(produced analogous to compounds V)

(c) Compounds of formula III

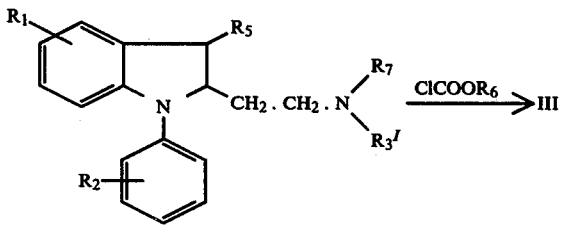

$R_7=CH_3$ or $CH_2.C_6H_5$ (produced analogous to process a), (d) Compounds of formula II wherein $R_3$ and $R_4=H$ may be alkylated to produce other compounds of formula II.

Insofar as the preparation of any starting material is not specifically described, this is known or may be effected in analogous manner to that described herein or to known methods.

Free base forms of the compounds of formula I may be converted into acid addition forms in conventional manner and vice versa. Suitable salts include the N-cyclohexyl-sulfamate, hydrochloride, maleate, fumarate, naphthalene-1,5-disulfonate, and oxalate salts. Salt formation with appropriate acids e.g. N-cyclohexylsulfamic acid and subsequent recrystallization may be conveniently used to separate cis/trans isomers.

The configuration (cis/trans) of each of the isomers wherein $R_5$ is alkyl may be determined in conventional manner, e.g. by x-ray spectroscopy for example of the methyl iodide salt or by n.m.r. spectroscopy.

In the following examples all temperatures are in degrees Centigrade and are uncorrected.

EXAMPLE 1:
3-methyl-1-phenyl-2-[2-(1-pyrrolidinyl)-ethyl]indoline
(process a)

1. A. solution of 83 g of sodium in 3 liters of liquid ammonia is made at −70° C. under nitrogen. 273 g of 3-methyl-1-phenyl-2-[2-(1-pyrrolidinyl)ethyl]indole in 3 liters of dry and peroxide-free tetrahydrofuran are added over a period of 15 minutes. The mixture is allowed to warm to −30° C. and stirred. The ammonia is refluxed. When the reaction is complete the ammonia is evaporated off and thereafter the mixture is allowed to warm to 20° over 30 minutes. 400 g solid ammonium chloride are added in portions to destroy excess sodium amide. The mixture is stirred for 10 minutes and 2 liters of saturated aqueous ammonium chloride are added under nitrogen over 30 minutes. 2 Liters of ether are added. The mixture is stirred, the organic layer separated off and dried over magnesium sulphate, and the solvent evaporated off to give the title compound (trans isomer) in crude free base form.

2. 170 g of this trans isomer in crude free base form in 1.7 liters of ethanol/water (9:1) are reacted with 199 g of N-cyclohexylsulfamic acid in 1.9 liters of ethanol/water (9:1). The mixture is left at 24° for 18 hours and then at 5° for 2 hours. The solid bis-(N-cyclohexylsulfamate) salt is collected and recrystallized from ethanol/water (9:1). M.pt. 158°–160°.

3. 169 g of this salt in 2 liters of toluene and 2 liters 2 N KOH are stirred at 25° for 15 minutes and then at 60° until the suspension clears up (ca. 5 minutes). The organic layer is separated off, and dried with magnesium sulphate, The organic solvent is removed to give the title compound (trans isomer) in free base form as an oil which is converted into the dihydrogen citrate salt. M.pt. 136°–138°. The hydrochloride salt has M.pt. 165°–170°. The methyliodide salt has M.pt. 250°–251°.

The starting material is obtained as follows:
(a) 330 g of 1,1-diphenylhydrazine hydrochloride, 211 ml of methylethylketone and 3.6 liters of acetic acid are heated to 80° over 1 hour under nitrogen and under stirring. The mixture is maintained at 80° for 1.5 hours, cooled and water (4 liters) added thereto. Toluene (3 times 1.5 liters) is added to extract the 2,3-dimethyl-1-phenylindole. The organic extracts are washed with water and filtered through silicagel to give, after evaporation of the toluene, the product as an oil.

(b) To a solution of 310 g of 2,3-dimethyl-1-phenylindole in 170 ml 40% formaldehyde and 1.6 liters acetic acid there is added dropwise 175 ml pyrrolidine at such a rate that the mixture temperature is 55° to 60°. When the addition is complete the mixture is stirred for 15 minutes and treated at 55° to 60° for 2 hours. 1.6 liters of water are added. The mixture is extracted with toluene (five times 1.6 liters), and the extracts are carefully washed with two 1.6 liter portions of 2 N NaOH. The solution is dried with 100 g of magnesium sulphate and the solvent removed to give 3-methyl-1-phenyl-2-[2-(1-pyrrolidinyl)ethyl]indole as a brown oil which is treated with 7.5 liters of petroleum ether (B.pt. 90°–120°) and then filtered. The petroleum ether solution of 3-methyl-1-phenyl-2-[2(1-pyrrolidinyl)ethyl]indole is treated with hydrogen chloride gas to yield the hydrochloride salt. M.pt. 213°–216°. The free base is set free from the hydrochloride in toluene using 2 N NaOH and obtained as an oil.

EXAMPLE 2:
2-(2-dimethylaminoethyl)-3-methyl-1-phenylindoline

To a solution of 22.3 g of 2-(2-dimethylaminoethyl)-3-methyl-1-phenylindole in 160 ml of tetrahydrofuran there are added 6.1 g of sodium borohydride. 26.3 ml of boron trifluoride diethyl etherate are added dropwise at room temperature. The mixture is then heated at reflux for one hour, cooled to 0° and 15 ml of water are slowly added dropwise. The mixture is then poured onto ice-water and the resulting boron complex is extracted with ethyl acetate.

The extracts are washed with water and dried over sodium sulphate. The mixture is concentrated by evaporation to an oil and the residue is boiled in 40 ml of concentrated hydrochloric acid for one hour. The aqueous phase is made alkaline with sodium carbonate with cooling and is extracted with ethyl acetate. The washed and dried extract is then concentrated by evaporation and the title compound (cis isomer) in the oily residue is purified via salt formation. The hydrogen maleate has a M.pt. of 164°–167°.

EXAMPLE 3:
5-chloro-1-p-chlorophenyl-2-(2-dimethylaminoethyl)-3-methylindoline The title compounds are produced in analogous manner to Example 2, using 5-chloro-1-p-chlorophenyl-2-(2-dimethylaminoethyl)-3-methylindole as starting compound. The major product is the cis compound. M.Pt. of the hydrochloride: 187°–190°. The trans compound is isolated from the mother liquor. M.Pt. of the hydrochloride: 163°–168° (both from acetone).

EXAMPLE 4:
2-aminoethyl-3-methyl-1-phenylindoline

To a solution of 20 g of 2-aminoethyl-3-methyl-1-phenylindole in 160 ml of tetrahydrofuran, there are added dropwise at room temperature 9.6 g of borane/dimethyl sulphide complex. The mixture is stirred for 1.5 hours. Subsequently 20 ml of water are carefully added dropwise, the mixture is poured onto water and is extracted with diethyl ether. After washing with water and drying over sodium sulphate, complete concentration by evaporation is effected and the residue is heated at reflux in a mixture of 80 ml of n-propanol and 160 ml of concentrated hydrochloric acid for one hour. The mixture is then made alkaline with NaOH while cooling and is extracted with ethyl acetate. After the mixture is washed with water and dried over sodium sulphate, the solvent is distilled off and the oily residue is converted into the hydrogen maleate; M.Pt. 198°–201°. The salt is converted back into the base, the nuclear resonance spectrum of which shows that 90% of the title compound (cis isomer) are present having impurities of 10% of the trans isomer. The pure cis isomer may be made by repeated crystallization of the N-cyclohexylsulfamate salt.

The 2-aminoethyl-3-methyl-1-phenylindole used as starting material is produced as follows:

(a) 129 g of 1,1-diphenylhydrazine, 91 g of 2-oxobutyric acid ethyl ester and 7 ml of glacial acetic acid are heated to 100° for 15 minutes. The resulting solution is then added dropwise to 700 ml of a boiling ethanolic hydrochloric acid solution while stirring and the mixture is refluxed for 30 minutes. Upon cooling the mixture is poured onto ice-water and is shaken with diethyl ether. The organic extracts are washed with water and dried over sodium sulphate. The solvent is removed and the oily residue, 3-methyl-1-phenyl-2-indole carboxylic acid ethyl ester is used in the next stage without further purification. Rf:0.7 on silica gel, eluate: methylene chloride.

(b) To a suspension of 27.3 g of lithium aluminium hydride in 350 ml of tetrahydrofuran at reflux, there is added dropwise a solution of 195 g of 3-methyl-1-phenyl-2-indole carboxylic acid ethyl ester in 700 ml of tetrahydrofuran. After the addition refluxing is continued for a further 30 minutes, followed by cooling to 0°. 140 ml of a saturated aqueous sodium sulphate solution are added dropwise. Filtration is subsequently effected and the filtrate is completely concentrated by evaporation at reduced pressure. The oily residue is then chromatographed on silica gel for purification. Eluate: Hexane/ethyl acetate 1:1. Rf value of the oily 3-methyl-1-phenyl-2-inodolemethanol on silica gel: 0.25; eluate: ethyl acetate/pentane 2:8.

(c) To a mixture of 110 g of 3-methyl-1-phenyl-2-indole methanol in 230 ml of toluene and 9.2 g of calcium chloride there is introduced at room temperature hydrochloric acid gas for 10 minutes. Filtration is then effected, the solvent is distilled off at reduced pressure, whereupon the 2-chloromethyl-3-methyl-1-phenylindole remains as a reddish oil. The latter is used in the following step without further purification.

(d) The crude 2-chloromethyl-3-methyl-1-phenylindole is dissolved in 460 ml of methylene chloride. 2.3 g of tributylbenzylammonium bromide are added. A solution of 51.4 g of potassium cyanide in 79 ml of water is added and the mixture vigorously stirred for 4 hours at room temperature. The methylene phase is then separated, washed with water, dried over sodium sulphate and concentrated by evaporation. The oily residue, 3-methyl-1-phenyl-2-indole acetonitrile, is purified by chromatography on silica gel with methylene chloride. Rf on silica gel: 0.5; eluant: methylene chloride.

(e) To a solution of 83 g of 3-methyl-1-phenyl-2-indole acetonitrile in 340 ml of n-propanol there are added 100 ml of concentrated aqueous ammonia and two spoons of Raney nickel. The mixture is hydrogenated at 60° and normal pressure. After the hydrogen take-up is complete, filtration is effected and the filtrate is made slightly acid with glacial acetic acid under cooling. After the addition of water, washing with diethyl ether is effected and the aqueous phase is made alkaline with dilute ammonia. The latter is extracted with methylene chloride and the extract is concentrated by evaporation after washing with water and drying over sodium sulphate. The residue, 2-aminoethyl-3-methyl-1-phenylindole, is then converted into the hydrochloride. M.Pt. 202°–207° (from acetone/diethyl/ether).

EXAMPLE 5:
3-Methyl-2-(2-methylaminoethyl)-1-phenylindoline whereupon the ethyl carbamate of the trans-3-methyl-2-(2-methylaminoethyl)-1-phenylindoline remains as a brown oil. 2. The latter is dissolved in 17 ml of n-butanol. 3.5 g of pulverized potassium hydroxide are added. The mixture is heated for 4 hours in an oil bath at 110°.

After cooling, the mixture is poured onto water and is extracted with ethyl acetate. The organic phase is separated, dried over sodium sulphate and completely concentrated by evaporation. The oily residue, the title compound (trans isomer), is converted into the hydrochloride for purification. M.pt. 201°–205° (from ethanol).

The following compounds of formula I are also obtained in analogous manner:

| Ex  | $R_1$    | $R_2$    | $NR_3R_4$   | $R_5$       | Isomer | M.pt.      | Analogous to Ex |
|-----|----------|----------|-------------|-------------|--------|------------|-----------------|
| (a) | H        | H        | $N(CH_3)_2$ | $CH_3$      | trans  | 128–132°[1] | 1               |
| (b) | 5-$CH_3$ | p-$CH_3$ | $N(CH_3)_2$ | $CH_3$      | trans  | 162–169°[2] | 1               |
| (c) | 5-$CH_3$ | p-$CH_3$ | $N(CH_3)_2$ | $CH_3$      | cis    | 199–204°[1] | 2               |
| (d) | H        | H        | $NHCH_3$    | $CH_3$      | cis    | 175–177°[1] | 5               |
| (e) | H        | H        | $NH_2$      | $CH_3$      | trans  | 193–197°[4] | 1 or 4          |
| (f) | H        | H        | N⌒NCH₃      | $CH_3$      | cis    | 235–238°[5] | 2               |
| (g) | H        | H        | N⌒ (piperidine) | $CH_3$  | cis    | 169–171°[1] | 2               |
| (h) | H        | H        | N⌒NCH₃      | $CH_3$      | trans  | 223–228°[5] | 1               |
| (i) | H        | H        | N⌒ (hexahydro) | $CH_3$   | trans  | 136–140°[6] | 1               |
| (j) | H        | H        | N⌒ (hexahydro) | $CH_3$   | cis    | 184–187°[1] | 2               |
| (k) | 5-F      | p-F      | $N(CH_3)_2$ | $CH_3$      | cis    | 192–194°[1] | 2               |
| (l) | 5-$CH_3O$| p-$CH_3O$| $N(CH_3)_2$ | $CH_3$      | trans  | 203–204°[3] | 1               |
| (m) | H        | H        | $NH_2$      | H           | —      | 209–212°[2] | 1 or 4          |
| (n) | H        | H        | $N(CH_3)_2$ | H           | —      | 117–120°[1] | 1 or 4          |
| (o) | H        | H        | $N(CH_3)_2$ | $CH(CH_3)_2$| trans  | 131–134°[6] | 1               |
| (p) | H        | H        | $N(CH_3)_2$ | $CH(CH_3)_2$| cis    | 164–167°[1] | 2               |
| (q) | H        | H        | $N(CH_3)_2$ | $C_2H_5$    | trans  | 118–121°[1] | 1               |
| (r) | H        | H        | $N(CH_3)_2$ | $C_2H_5$    | cis    | 143–146°[1] | 2               |
| (s) | H        | H        | $NHCH_3$    | H           | —      | 188–191°[2] | 1 or 5          |
| (t) | H        | H        | N⌒ (pyrrolidine) | H      | —      | 169–171°[7] | 1               |

[1] hydrogen maleate
[2] hydrochloride
[3] bis[base] naphthalene-1,5-disulfonate
[4] oxalate (90% trans, 10% cis)
[5] bishydrogen fumarate
[6] hydrogen fumarate
[7] bis N-cyclohexylsulfamate (Process b)

(1) 7.5 ml of triethylamine are added to a solution of 5.0 g of trans-2-(2-dimethylaminoethyl)-3-methyl-1-phenylindoline in 36 ml of toluene. 2.6 ml of ethyl chloroformate are added dropwise whilst refluxing the reaction mixture. After one and two hours 2.6 ml of ethyl chloroformate are again added. After a reaction time of 3 hours, cooling is effected and the reaction mixture is distributed between methylene chloride and dilute hydrochloric acid. After the mixture is washed with water and dried over sodium sulphate, the solvent is removed, Further compounds of formula I may be produced wherein $R_5$ is n-$C_4H_9$ and $R_1$ is 4, 6 or 7-n$OC_4H_9$, $R_2$ is o- or m-$OC_4H_9$ and $NR_3R_4$ are

The compounds of the invention are useful because they exhibit pharmaceutical activity in animals. In particular the compounds are useful anti-diabetic and anti-obesity agents as indicated in that the compounds prevent an increase in the blood sugar level in animals following an oral starch load.

In one test male Wistar rats in groups of 4 which are fasted for 16 hours are given an initial dose of from 25 to 200 mg/kg p.o. of the test compound. One hour later, the rats are given 2.5 grams per kilogram of animal body weight of starch load. Thirty minutes after administration of the starch, the rats are anaesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliters). The heparinized blood is used to determined the blood sugar level with an autoanalyzer. The blood sugar content is compared to the control group which receives 0.5% carboxymethyl cellulose and an oral starch load and are run concurrently.

In another test four male fasted Cebus monkeys (2.0–2.3 kg in body weight) are administered with the compounds suspended in 0.5% carboxymethyl cellulose at a dose of from 3 to 100 mg/kg animal body weight p.o. One hour later, an oral starch load (1.5 g/5 ml/kg) is given and then the blood sugar level in the blood is determined 30, 45, 60, 90, 120, 180 and 240 minutes thereafter as described above.

For the above uses the effective dose of active ingredient employed may vary depending on the particular compound employed, the mode of administration and the severity of the condition being treated. However, in general, satisfactory results are obtained when the compounds of the invention are administered at a daily dosage of from about 0.6 milligrams to about 200 milligrams per kilogram of animal body weight, preferably given in divided doses two to four times a day, or in sustained release form. For most larger mammals, the total daily dosage is from about 40 to about 2000 milligrams. Dosage forms suitable for internal use comprise from about 10 to about 1000 milligrams of the active compound in intimate admixture with a solid or liquid pharmaceutically acceptable carrier or diluent.

The compounds of the invention may be administered in pharmaceutically acceptable acid addition salt form. Such acid addition salt forms exhibit the same order of activity as the free base forms and are readily prepared in conventional manner. The present invention also provides a pharmaceutical composition comprising a compound of the invention, in free base form or in pharmaceutically acceptable acid addition salt form, in association with a pharmaceutical carrier or diluent. Such compositions may be in the form of, for example, a solution or a tablet.

The example 1 compound exhibits particularly interesting activity.

In a group of compounds $R_3$ and $R_4$ are independently hydrogen or alkyl($C_{1-6}$) or together with the nitrogen atom to which they are bound form a pyrrolidino, piperidino, morpholino or 4-alkyl($C_{1-4}$)piperazino radical.

In a 1st group of compounds $R_3$ is hydrogen.
In a 2nd group of compounds $R_3$ is alkyl.
In a 3rd group of compounds $NR_3R_4$ is pyrrolidino.
In a 4th group of compounds $NR_3R_4$ is piperidino.
In a 5th group of compounds $NR_3R_4$ is morpholino.

In a 6th group of compounds $NR_3R_4$ is 4-alkyl-$C_{1-4}$piperazinyl.
In a 7th group of compounds $R_5$ is alkyl.
In a 8th group of compounds $R_5$ is methyl.
In a 9th group of compounds $R_5$ is hydrogen.

We claim:

1. A compound of formula I

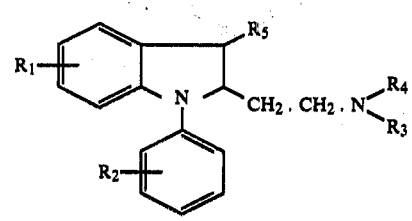

wherein
$R_1$ and $R_2$ independently are hydrogen, halogen of atomic number from 9 to 35, alkoxy ($C_{1-4}$) or alkyl ($C_{1-4}$),
$R_3$ and $R_4$ either are independently hydrogen or alkyl ($C_{1-6}$), or together with the nitrogen atom to which they are bound form a pyrrolidino, piperidino, perhydrazepino, morpholino or 4-alkyl($C_{1-4}$)piperazinyl radical, and
$R_5$ is hydrogen or alkyl($C_{1-4}$),
or a pharmaceutically acceptable acid addition salt thereof.

2. A pharmaceutical composition comprising an anti-diabetic or anti-obesity effective amount of a compound of claim 1 in association with a pharmaceutical diluent or carrier.

3. A method of treating diabetes or obesity in animals which comprises administering a therapeutically effective amount of a compound of claim 2 to an animal in need of such treatment.

4. A compound of claim 1 which is 3-methyl-1-phenyl-2-[2-(1-pyrrolidinyl)-ethyl]indoline or a pharmaceutically acceptable acid addition salt thereof.

5. A compound of claim 4 which is trans-3-methyl-1-phenyl-2-[2-(1-pyrrolidinyl)-ethyl]indoline.

6. A compound of claim 1 where $R_1$ and $R_2$ represent H, $NR_3R_4$ represents $N(CH_3)_2$ and $R_5$ represents $CH_3$.

7. A compound of claim 1 wherein $R_1$ represents 5-$CH_3$, $R_2$ represents p-$CH_3$, $NR_3R_4$ represents $N(CH_3)_2$ and $R_5$ represents $CH_3$.

8. A compound of claim 1 wherein $R_1$ and $R_2$ represent H, $NR_3R_4$ represents

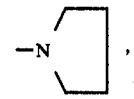

$R_5$ represents $CH_3$, and the compound is of cis-configuration.

9. A compound of claim 1 where $NR_3R_4$ represents pyrrolidino.

10. A compound of formula I

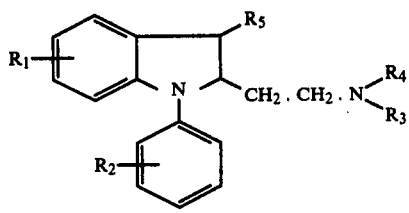

wherein $R_1$ and $R_2$ independently are hydrogen, halogen of atomic number from 9 to 35, alkoxy ($C_{1-4}$) or alkyl ($C_{1-4}$), $R_3$ and $R_4$ either are independently hydrogen or alkyl ($C_{1-6}$), or together with the nitrogen atom to which they are bound form a pyrrolidino, piperidino, morpholino or 4-alkyl($C_{1-4}$)piperazinyl radical, and $R_5$ is hydrogen or alkyl($C_{1-4}$), or a pharmaceutically acceptable acid addition salt thereof.

11. A compound of claim 1 wherein $NR_3R_4$ represents piperidino.

12. A compound of claim 1 wherein $R_5$ is methyl.

* * * * *